US00PP18796P2

(12) United States Plant Patent
Saville et al.

(10) Patent No.: US PP18,796 P2
(45) Date of Patent: May 6, 2008

(54) ROSE PLANT NAMED 'SAVIBUNDA'

(50) Latin Name: *Rosa hybrida*
Varietal Denomination: SAVibunda

(75) Inventors: Lillian Saville, Peabody, MA (US); Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/514,661

(22) Filed: Sep. 1, 2006

(51) Int. Cl.
*A01H 5/00* (2006.01)

(52) U.S. Cl. ..... Plt./145

(58) Field of Classification Search ..... Plt./145
See application file for complete search history.

*Primary Examiner*—Anne Marie Grunberg
*Assistant Examiner*—S. B. McCormick-Ewoldt

(57) ABSTRACT

'SAVibunda' is a new and distinct variety of floribunda-type rose plant primarily identified by its light yellow flowers on a highly disease resistant and well formed bush. It has survived abnormally cold winters in zone 5a, yet seems to flower and do well in the heat of zone 9b. This new cultivar would make an excellent, low maintenance border plant or specimen plant. The flowers are long lasting on the plant and as cut flowers.

1 Drawing Sheet

CROSS REFERENCE

This present invention can be compared to 'SAVapam' (U.S. Plant Pat. No. 17,329) from this same hybridizing program. 'SAVapam' is a mini-flora with flowers of a light pink blend and this new invention is a floribunda with flowers of light yellow. Although different in size, both plants tend to have the same plant habit: both being upright with uniform branching and a rounded crown; good tolerance for both heat and cold; and above average hardiness and disease resistance. The color of the foliage is the same on both cultivars. 'SAVapam' and this new cultivar, 'SAVibunda', share the same seed parent of 'MORpoly' (U.S. Plant Pat. No. 8,453).

RIGHTS TO THE INVENTION

Be it known that the actual selection and crossing of pollen and seed parents for this new and improved cultivar were performed by Lillian Saville, now of Peabody, Mass. Wendy R. White of Ipswich, Mass., performed selection of this particular seedling and subsequent evaluations and propagations.

Genus and species: *Rosa hybrida.*

Varietal denomination: 'SAVibunda'.

BACKGROUND OF THE INVENTION

This present invention relates to a new and distinct variety of hardy, bush type plant of the floribunda rose class. This new variety was created by Lillian Saville under controlled conditions in a greenhouse in Rowley, Mass., in June of 1996 by artificially pollinating the seed parent 'MORpoly' (U.S. Plant Pat. No. 8,453) with pollen from 'KORresia' (U.S. Plant Pat. No. 3,509, expired).

Idyllic goals of this breeding program were to produce unique, diminutive size roses with good vigor, disease resistance and hardiness along with fragrance and abundant, hybrid tea type, exhibition form blooms throughout the growing season. Roses chosen as pollen and seed parents for this program are chosen for having 2 or more of the qualities of hybrid tea, exhibition form; abundance of bloom; vigor; disease resistance; hardiness; fragrance. These roses are crossed with miniature roses having, primarily, abundant bloom production and any other of those additional qualities. In an attempt to breed toward this end, 'MORpoly' was selected for its diminutive size, abundance of yellow blooms with little fade, and its vigor. The pollen parent selected. 'KORresia', was selected because it is vigorous and hardy, with good bloom production, above average disease resistance and fragrant, non-fading yellow flowers. Ten seedlings resulted from this cross but this new cultivar is the only one selected out for further evaluation. Although this new invention is not a miniature or mini-flora rose, it appeared to have qualities we wanted to use in further hybridizing. Outside testing has shown it has vigor, abundance of bloom, extreme hardiness and excellent disease resistance.

This present invention bares resemblance to its parents. Traits specifically from its seed parent are its vigor and branching plant habit. From its pollen parent are form and size of flowers and foliage. Flowers of both the seed parent and pollen parent are a darker yellow than this new invention. Additionally, the most notable difference from its seed parent is size, 'MORpoly' being of the miniature rose class and this new invention being a much larger floribunda. Other than deepness of color, differences from its pollen parent are in the plant habit, with 'KORresia' being more upright, and in flower form, the new invention being more cupped, especially in the newly opened bloom.

SUMMARY OF THE INVENTION

This present invitation relates to a new and distinct variety of hardy, bush type rose plant of the floribunda class. The characteristics distinguishing it from its parents and all other varieties of which I am aware are its tremendous disease resistance and extreme hardiness in a light yellow rose of the floribunda class. Other distinguishing characteristics are its abundance of bloom; the loose, informal form of its light yellow flowers; flowers that last well as cut flowers; those flowers borne singly on long stems and in both small and large, loose sprays; its branches spreading in such a manner as to give the mature plant a rounded shape; its ability to set hips easily.

Successive asexual reproduction by cuttings of this new cultivar in Rowley, Mass., and Arroyo Grande, Calif., has shown that all distinguishing characteristics of this rose continually come true to form.

BRIEF DESCRIPTION OF THE DRAWING

The accompanying color photograph was taken of leaves, stems and flowers in all stages of development and also of newly forming hips, from plants of this new cultivar that were grown outdoors in the ground in July in Essex County, Mass.

BOTANICAL DESCRIPTION OF THE PLANT

The following observations, measurements, values and comparisons describe 7 year old plants of *Rosa hybrida.* 'SAVibunda', of the floribunda rose class, grown outdoors in the ground in a sandy loam in Essex County, Mass., where they receive additions of granular chemical fertilizers twice during the growing season; and from 7 year old plants grown in amended sandy soil in San Luis Obispo County, Calif., where they received liquid fertilizer once or twice a week depending on climatic conditions; as well as observations of a single 7 year old plant grown in a plastic covered greenhouse, in a white 5 gallon bucket where it received a near constant supply of a low dosage of liquid fertilizer during the growing season in Essex County, Mass. When there is a distinguishable difference between the plants in the different locations, it is so noted. Color References are made using The Royal Horticultural Society Colour Chart, except where common terms of color are used.

Parentage: 'MORpoly' (U.S. Plant Pat. No. 8,453) as the seed parent by 'KOResia' (U.S. Plant Pat. No. 3,509, expired) as the pollen parent.

Botanical classification: *Rosa hybrida.*

Varietal denomination: 'SAVibunda'.

Commercial class: Floribunda.

FLOWERS

Blooming habit: This new invention is a repeat bloomer. When blooms were removed on the greenhouse grown plant before they began to fade, the mature plant had a quick repeat bloom cycle of sixteen to twenty-one days. Mature outdoor grown plants may have three to four weeks between bloom cycles.

Borne: Buds and flowers are borne singly and also in small sprays of two or three and large, loose sprays of up to seven. Sprays are usually on long canes that originate near the base of the plant. Usually the longer canes have the larger sprays. Flowers borne singly are most often found on stems originating from branched canes.

Bud size is 15/32- to ½-inch in diameter and ⅝-inch high. The form is obtuse with an acute apex and rounded-truncate base. Color where the sepals first divide is near 14D, Chrome Yellow.

Sepals: The color of the basal area of the outside surfaces is a medium yellow-green, near 144B; on the tips and extensions it is a very dark yellow-green, near 147A; the area in between is a blend of those two. The surface is semi-glossy near the base and becoming matte for the upper third and the extensions. The inside surface appears a medium yellow-green, near 146D, with a fine pubescent covering from the base increasing to a slightly thicker pubescent covering on the upper third. The shape of the sepals is oval-oblong with an acuminate apex and truncate base. The width is most often between ¼- and 5/16-inch wide. Outer sepals are usually between ⅞- and 1-inch long and may have a single linear, foliar appendage along one or both margins. Inner sepals average ¾-inch long with no foliar appendages. Sepals roll back just ahead of the petals. They do not drop with the petals and return to an upright position as the hip forms.

Receptacles are urn shaped and their surfaces are glabrous and matte. The diameter is ¼-inch and the height is ¼-inch. Color is near 145A, a medium shade of yellow-green. The top-most surface of the receptacle is circular and a very light green-yellow, nearest 1C, also with a glabrous surface.

Peduncle length is variable. When borne singly they are over one inch long, usually around 1¼-inches. When borne in sprays they are usually less than an inch long with their lengths varying from 11/16- to ⅞-inch. The diameter averages 7/64-inch, varying between 3/32- and ⅛-inch. The color is near 146D, a little darker yellow-green than the receptacle. The aspect is erect and the strength is strong. When young, the surface is matte and coarse. As the hips begin to form, small, stiff hairs and stipitate glands become visible. At the base of the peduncle are 2 opposite appendages; one is usually a lanceolate, foliar appendage, and the other may be a 2- or 3-leaflet leaf or another lanceolate foliar appendage.

Bloom: The size of fully expanded blooms borne singly is 2¾- to 3¼-inches across and 1½-inches deep. When borne in sprays the fully expanded blooms measure 1⅞- to 2 3/16-inches across and 1 1/16-inch deep. The form tends to be high centered at first with a convex upper profile and a flattened convex lower profile; full open it has a flattened convex upper profile and an arched lower profile. Fragrance is sweet and mild.

Petalage under normal conditions varies between 31 and 41 and the quantity of petaloids varies from 2 to 11. The quantity of petaloids has no relationship to the quantity of petals.

Petals are velvety on the upper surface and satiny on the lower surface. They are of medium thickness and both surfaces are glabrous. The form is nearly round with an acute apex located at the tip of the central vein. The outer petals have a rounded truncate upper margin and a notch adjacent to each side of the apex. On one side of this apical area there is often a serrature with its tip pointing toward the apex, characteristically creating a fold in the margins of mature outer petals. On the intermediate petals the outer margin is more rounded and has a shallow, rounded to deep notch on only one side of the apex causing the outer margins to appear cordate. The margins of the inner petals may have 2 serratures to one side of the apex with their tips pointing toward the apex giving them a rippled appearance. The base of the petals is broad-rounded with a shallow, rounded notch on one side of, or at, the point of attachment.

Color during the first few days along the margins of the outer petals is near 12D, a light Aureolin Yellow. The rest of the exposed petal area is near 14D, a light Chrome Yellow, with a blending between these two areas. The Basal area is near 12B, a darker Aureolin Yellow. The point of attachment is a deep yellow, near 7A. The reverse of these petals is a light Chrome Yellow, between 15D and 14D. The basal area is a medium yellow, between 14C and 13C. At the point of attachment the color is medium yellow, near 4B. The inner petals are near 11B, with the point of attachment and basal area near 12B and blending up and into the rest of the petal surface. The reverse is near 12C, a medium Aureolin Yellow, with the point of attachment and basal area of near 12B, and blending up and into the 12C.

When the flower is full open, the marginal area of the outer petals is between 11D and 13D, blending in with a color near 11B from the basal area. The point of attachment is near 11A. The reverse is near 11D and near 5A, Dresden Yellow, at the point of attachment. The intermediate petals are near 13D, with a basal area near 10C, Barium Yellow, which blends up into the near 13D of the rest of the petal, with near 6B, Sulphur Yellow, at the point of attachment. The reverse is also near 13D with the basal area of near 10C blending in and 7B, a medium yellow, at the point of attachment. The inner petals are near 13D, with near 8A at the point of attachment. The reverse of the inner petals is the same as their upper surface, near 13D and 8A at attachment.

Petals generally fade uniformly to a very light yellow, near 11D, before they drop cleanly from the plant. The process from when sepals reflex to fully opened flower may take 5 to 8 days with an additional 4 to 6 days to full fade just before the petals drop. Cut flowers can last 6 to 10 days.

Petaloids vary in width from ½-inch to 1¼-inches. Some are attached to a filament and some are folded over. Some have an anther at the apex or along the margin of one side. Some are just small narrow petals. They range from 3/16-inch long to 11/16-inch long whether they are attached directly, or by a filament and whether or not they have an anther attached.

REPRODUCTIVE ORGANS

Stamens are arranged in single or near-double rows around the upper, outer edge of the receptacle. The following measurements were taken on 3-day open flowers as grown outdoors in San Luis Obispo County, Calif. The quantity of Stamens on those flowers was between 102 and 108. (As an example, the one bloom counted having 102 stamens had an additional 7 incomplete anthers attached to petaloids; the one with 108 stamens did not have any of these incomplete anthers. Those others counted had similar totals of stamens plus incomplete anthers.) Filaments are near 2B, a medium chartreuse-yellow, at the base with the upper portion nearest 12A, Aureolin Yellow, and are translucent. The length is near ¼-inch. The color of the Anthers is near 21D, Maize Yellow. The color of the Pollen sacs around the anther is near 21A, Saffron Yellow. When dried, the color of the Pollen is a medium to light yellow, Amber Yellow, near 18A. The amount is ample.

There are about 60 Pistils on these flowers. The Styles are not very thin and are slightly undulate. These observed were not strong; sometimes two are conjoined part way up or all the way to the top. The color of the Styles is near 2D with approximately the upper third near 29C, Carrot Red. The color of the Stigma is near 4D, a light Primrose Yellow.

Hips are near pear shape. The surface is semi-glossy and glabrous. The colors of the hips when mature, as grown outdoors in San Luis Obispo County were near 169A and near 169B. Seeds do not protrude from the top. Those grown in San Luis Obispo County, Calif., had a diameter, at the widest part of 25/32- to 15/16-inch wide at the widest part with a height of 15/16- to 1 1/32-inches. Measurements of mature hips as grown outdoors in Essex County, Mass., were 9/16-inch wide by 11/16-inch tall. Immature hips grown in Essex County, Mass., may be seen in the accompanying color photograph.

PLANT

Plant habit of this new invention is upright, uniformly and well-branched, with a rounded crown, growing to a height of thirty-six to thirty-eight inches with a width of two to three feet. Growth is vigorous. Disease resistance is excellent against all major rose diseases. Resistance to insects is above average. The length of the flowering stems is generally between 4½- to 7¾-inches when born in clusters and 8- to 13-inches when borne singly.

Leaves are pinnately compound with five leaflets except for three-leaflets leaves immediately below the peduncle and at the base of the stems. Mature leaves from plants grown in San Luis Obispo County, Calif., measured from 5⅞- to 6⅜-inches from point of attachment at the stem to the apex of the terminal leaflet. Mature leaves from plants grown outdoors in Essex County, Mass., measured 5⅛- to 5¾-inches long. Leaflets are narrow-ovate with an oval base and an acuminate apex on the terminal leaflet and acute apices on the lateral leaflets. Margins are simply and finely serrated with a gland at the tip of each serrate. Terminal leaflets in San Luis Obispo, Calif., measured 2 15/16- to 3-inches long and 1½- to 1⅝-inch in width at their widest part. Outdoors in Essex County, Mass., the terminal leaflets measured 2¼- to 2¾-inches long and 1½-inches wide. All veins are recessed on the adaxial surface with the main vein being entirely recessed and increasingly smaller veins are increasingly less recessed. On the abaxial surface, the main vein protrudes significantly, the primary lateral veins protrude only slightly and the remainder of the veins are flush with the leaflet surface.

Color of the new foliage is near 146A, a dark yellow-green, flushed with and margins of near 180A from the Greyed-Red group. The abaxial surface is near 146B and heavily flushed with near 185A, Chrysanthemum Crimson. Older foliage has no anthocyanin coloring. In San Luis Obispo County, the adaxial surface of the old foliage is a very dark yellow-green, near 147A, and the abaxial surface is near 147B. In Essex County, Mass., the old foliage is near 139A, a dark green, and the abaxial surface is a green color between 137B and 147B. It has been further observed in Berkshire, Hampden and Essex Counties in Massachusetts that when it was passed time for the addition of fertilizer, the new growth was a much lighter shade of yellow-green, between 144A and 144B.

New leaves have a semi-glossy surface. Older foliage is matte. Adaxial surface is glabrous and the abaxial surface is leathery with the main vein completely protruding and the primary lateral veins just barely protruding. The edges have a simple serration that becomes very fine near the base of the leaflets.

Petioles vary from 1 1/16- to 1 7/16-inches long with a diameter of 3/32- to 3/16-inch. On younger foliage the abaxial surface is between 144A and 145B and may be suffused with a color near 184D from the Greyed-Purple Group. On the adaxial surface, the ridges are the same color as the upper leaf surface, the groove is near 145A, and both are suffused with near 184A. On the mature leaves the color of the abaxial side gradates from near 146D at the base to near 146C where it attaches to the rachis. Along the ridge of the adaxial surface the color is near 147B at the base of the petiole gradating to near 147A where it attaches to the rachis. Likewise, the groove gradates from a color between 146D and 194C at the base to near 146C where it attaches to the rachis. The surface of the groove is pilose and hairs are most numerous near the juncture with the rachis. There are a few stipitate glands near and along the ridges. There are only a few hairs along the abaxial surface.

Stipules are paired at the base of the petiole with about ⅝-inch attached and a 3/16-inch attenuate tip angled out at 45° or more from the petiole. The color of the adaxial side is near 146B. The color of the abaxial side is near 146C. Margins on the attached portion of the stipule are lined with numerous, near evenly spaced stipitate glands. Margins on the tip that is angled outward have slightly fewer glands and they are not as near evenly spaced.

The Rachis is about 1⅛-inches long. On younger foliage the abaxial surface is between 145A and 144B and suffused with near 184A. On the adaxial surface, the ridges are the same color as the upper leaf surface, the groove is near 145A, and both are suffused with a Greyed-Purple, near 184A. On older foliage the abaxial side is the near 146C. On the adaxial surface, the ridges are the same color as the upper leaf surface and the groove is near 147C. The groove is pilose and hairs are more numerous near junctures with the petiolules. There are a few stipitate glands near and along the ridges. There are considerably more hairs along the abaxial side of the rachis than that of the petiole.

Petiolules to the terminal leaflets vary from 15/16- to 1-inch. The length of the petiolules to the lateral leaflets is ⅛-inch. The adaxial surface has a few hairs in the groove only at the juncture with the rachis and there are very few stipitate glands along or near the ridge. There may be a few hairs on the abaxial surface only near the juncture with the rachis. The color of the adaxial surface of the petiolule is the same as the rachis, with that color extending into the main and primary lateral veins. The abaxial surface is a lighter yellow-green, near 146D on mature leaves and between 146D and 145B and suffused with near 181D on younger leaves, and extending into the main vein and primary laterals on the undersides of the leaflets. Smaller veins may appear darker.

Flowering stems can vary in length between eight and thirteen inches, when borne singly. Some of the growth of this new invention is candelabra-style, with stems originating at or below the ground, reaching straight up and terminating with a spray of flowers at the crown of the plant. The diameter of Main Canes is between ⅜- and 15/16-inch. Primary laterals have a diameter between 3/16- and ¼-inch. Flowering stems have a diameter of 5/32-inch.

New wood is glabrous and a medium green between 137C and 144A. Old wood is a darker and more of a yellow-green, near 146A. The surface is glabrous until lenticels begin to from near the base of the main canes, generally after the fourth or fifth year of growth.

Prickles: Main canes generally have no prickles. Primary laterals have from three to twelve prickles in 3½-inches of stem length. Flowering stems have between two and fourteen prickles on their entire length, usually concentrated in the lower third of the stem, and the quantity of these prickles is not relative to the length of the flowering stem. Flowering stems from a spray usually do not have prickles. On young growth the prickles are attenuate with a straight lower profile and slightly concave upper profile. On the older canes they are deltoid with a concave upper and lower profile. The color of the older prickles is a dark reddish-brown, between 175B and 200D. Mature prickles are usually ⅜-inch long. The shape of the base is narrow-oblong, 5/16-inch long by 5/32-inch wide. On flowering stems the length of the prickles usually ranges from ⅛- to 5/16-inch.

Hardiness: This new cultivar has been tested winter hardy and heat tolerant in USDA zones 5a to 9b.

It is claimed:

1. A new and distinct variety of hardy, floribunda-type rose plant is claimed, substantially as illustrated and described, with long lasting flowers of a very light yellow borne on a vigorous and upright growing plant with dark green foliage and excellent disease resistance, suitable for use as a garden perennial, border plant or large container plant.

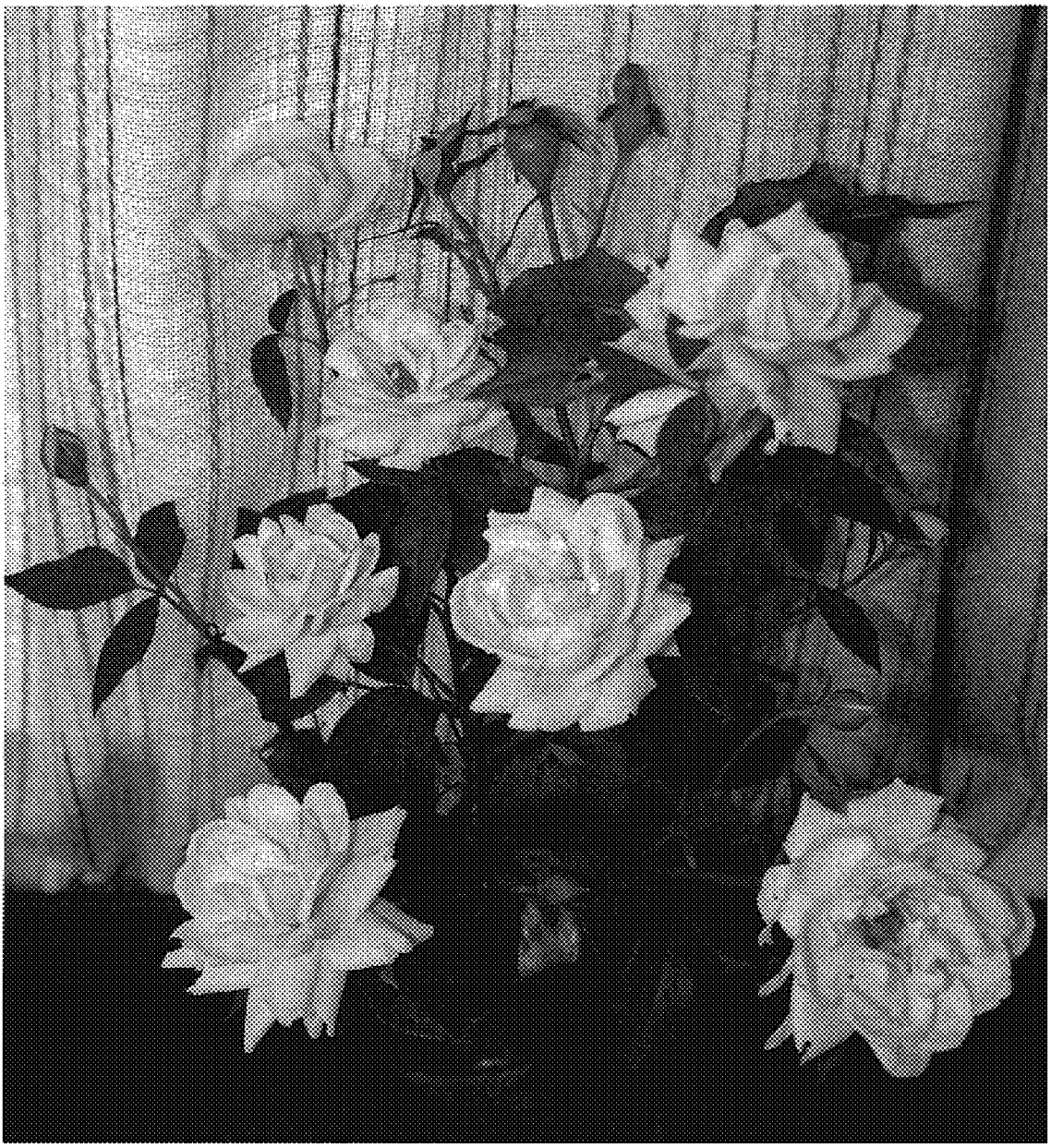

* * * * *